United States Patent [19]

Zajaczkowski

[11] Patent Number: 5,726,250
[45] Date of Patent: *Mar. 10, 1998

[54] COVALENTLY CROSSLINKED WATER-ABSORBENT GRAFT COPOLYMER

[75] Inventor: Michael J. Zajaczkowski, Yoe, Pa.

[73] Assignee: Adhesives Research, Inc., Glen Rock, Pa.

[*] Notice: The term of this patent shall not extend beyond the expiration date of Pat. Nos. 5,395,307 and 5,508,367.

[21] Appl. No.: 612,260

[22] Filed: Mar. 7, 1996

Related U.S. Application Data

[63] Continuation-in-part of Ser. No. 399,876, Mar. 7, 1995, Pat. No. 5,508,367, which is a continuation-in-part of Ser. No. 272,827, Jul. 11, 1994, Pat. No. 5,395,907.

[51] Int. Cl.$^6$ ................................................ C08F 220/26
[52] U.S. Cl. ........................... 525/296; 525/283; 525/301; 525/326.9
[58] Field of Search .......................... 525/283, 296, 525/301, 326.9

[56] References Cited

U.S. PATENT DOCUMENTS

| | | |
|---|---|---|
| 2,838,421 | 6/1958 | Sohl . |
| 3,096,202 | 7/1963 | De Groot Von Arx . |
| 3,152,940 | 10/1964 | Abel et al. . |
| 3,321,451 | 5/1967 | Gander . |
| 3,441,430 | 4/1969 | Peterson . |
| 3,556,835 | 1/1971 | Sorell . |
| 3,660,147 | 5/1972 | Van Hoof et al. . |
| 3,763,117 | 10/1973 | McKenna, Jr. et al. . |
| 3,786,116 | 1/1974 | Milkovich et al. . |
| 3,832,423 | 8/1974 | Milkovich et al. . |
| 3,842,058 | 10/1974 | Milkovich et al. . |
| 3,842,059 | 10/1974 | Milkovich et al. . |
| 3,842,146 | 10/1974 | Milkovich et al. . |
| 3,865,770 | 2/1975 | Blake . |
| 3,890,292 | 6/1975 | Bohme et al. . |
| 3,896,161 | 7/1975 | Borden et al. . |
| 4,033,918 | 7/1977 | Hauber . |
| 4,140,115 | 2/1979 | Schonfeld . |
| 4,170,582 | 10/1979 | Mori et al. . |
| 4,239,671 | 12/1980 | Fink et al. . |
| 4,310,509 | 1/1982 | Berglund et al. . |
| 4,341,680 | 7/1982 | Hauber et al. . |
| 4,388,432 | 6/1983 | Eskay . |
| 4,413,080 | 11/1983 | Blake . |
| 4,413,082 | 11/1983 | Gleichenhagen et al. . |
| 4,442,258 | 4/1984 | Sunakawa et al. ........... 524/767 |
| 4,499,896 | 2/1985 | Heinecke . |
| 4,554,324 | 11/1985 | Husman et al. . |
| 4,569,960 | 2/1986 | Blake . |
| 4,685,455 | 8/1987 | Vrouenraets . |
| 4,842,597 | 6/1989 | Brook . |
| 4,871,812 | 10/1989 | Lucast et al. . |
| 4,931,282 | 6/1990 | Asmus et al. . |
| 4,952,655 | 8/1990 | Seelmann-Eggebert et al. . |
| 4,992,501 | 2/1991 | Hanninen et al. . |
| 5,045,601 | 9/1991 | Capelli et al. . |
| 5,064,652 | 11/1991 | Bay . |
| 5,084,348 | 1/1992 | Czech et al. . |
| 5,088,483 | 2/1992 | Heinecke . |
| 5,094,912 | 3/1992 | Deibig et al. . |
| 5,098,962 | 3/1992 | Bozich . |
| 5,102,733 | 4/1992 | Zawadzki . |
| 5,125,995 | 6/1992 | D'Haese et al. . |
| 5,141,810 | 8/1992 | Ranade et al. . |
| 5,153,040 | 10/1992 | Faasse, Jr. . |
| 5,160,315 | 11/1992 | Heinecke et al. . |
| 5,183,664 | 2/1993 | Ansell . |
| 5,183,841 | 2/1993 | Bernard . |
| 5,196,504 | 3/1993 | Scholz et al. . |
| 5,229,447 | 7/1993 | Miyamjima et al. . |
| 5,270,111 | 12/1993 | D'Haese et al. . |
| 5,296,512 | 3/1994 | Beier et al. . |
| 5,319,020 | 6/1994 | Rosenski et al. . |
| 5,326,644 | 7/1994 | Scholz et al. . |
| 5,332,607 | 7/1994 | Nakamura et al. . |
| 5,380,779 | 1/1995 | D'Haese . |
| 5,389,376 | 2/1995 | Duan et al. . |
| 5,395,907 | 3/1995 | Zjaczkowski . |
| 5,407,717 | 4/1995 | Lucast et al. . |
| 5,468,821 | 11/1995 | Lucast et al. . |
| 5,508,367 | 4/1996 | Zajaczkowski ........... 526/320 |
| 5,578,683 | 11/1996 | Koch et al. ................ 525/301 |

FOREIGN PATENT DOCUMENTS 063 037 A2  10/1982  European Pat. Off. .

OTHER PUBLICATIONS

J. Brandrup et al. Polymer Handbook, 2d Ed., Wiley, New York, 1975, pp. III–144, III–148, VII–I, VII–2.
Chemical Abstracts 100:52757e.

*Primary Examiner*—Mark Nagumo

[57] ABSTRACT

A covalently crosslinked absorbent graft copolymer is provided comprised of a water-soluble base monomer and a water-soluble or water-dispersible macromer. In a preferred embodiment, the water-soluble base monomer comprises a carboxylic hydroxyalkyl ester monomer and the water-soluble macromer comprises an ethoxylated or propoxylated hydroxyalkyl (meth)acrylate. The covalently crosslinked absorbent graft copolymer exhibits desirable water absorbency and water vapor transmission rates and may be used in a variety of medical applications such as a wound dressing, medical adhesive or biomedical electrode.

26 Claims, No Drawings

COVALENTLY CROSSLINKED WATER-ABSORBENT GRAFT COPOLYMER

CROSS-REFERENCE TO RELATED APPLICATIONS

The present application is a continuation-in-part application of application Ser. No. 08/399,876, filed Mar. 7, 1995, now U.S. Pat. No. 5,508,367 which is a continuation-in-part of application Ser. No. 08/272,827, filed Jul. 11, 1994, now U.S. Pat. No. 5,395,907, issued Mar. 7, 1995.

BACKGROUND OF THE INVENTION

The present invention is directed to a crosslinked water absorbent graft copolymer.

There is an ongoing need in the medical industry for a pressure sensitive adhesive for long-term skin applications. An adhesive possessing this quality would be ideal for applications in which a patient's skin is wetted as a result of either site preparation or the accumulation of moisture under the adhesive during normal perspiration. This type of system could readily be used for surgical drapes, wound dressings, or other special applications in which durable bonding to saturated skin tissue is needed. It has been difficult to find an effective adhesive product to meet these demanding needs.

Adhesives exhibiting such properties can also be used with advantage as a biomedical electrode if made sufficiently conductive without the need to incorporate significant amounts of ionic or polar solutions into the adhesive which may result in phase separation and failure of the adhesive.

To meet the criteria described above, an adhesive must possess certain inherent qualities that are related to the chemistry of the adhesive. The design of such an adhesive should include a balance of moisture absorbent capabilities and adequate pressure sensitive adhesive properties. Hydrophilic character will enable the adhesive to interact with moisture and free up bonding sites at the adhesive/skin interface. Advantageously, not only will such an adhesive system readily absorb moisture at the skin-adhesive interface, but the adhesive will also serve as an effective vehicle to transport absorbed moisture in the form of water vapor from the adhesive to the ambient environment. This will allow for intimate contact of the adhesive with the skin.

Consideration must also be given to the safety of the adhesive. The adhesive must be non-toxic if it is to be used for medical purposes. This is especially true when bond sites are near open wounds or abrasions. An ideal long-term wound care adhesive or biomedical electrode should contain no extractables such as unreacted monomers, additives, or soluble polymeric systems. Such extractables could break down when exposed to solvents such as water. Absorption into skin, or migration to an open wound, may produce harmful effects to the patient. Therefore, it is important for the adhesive to maintain chemical integrity throughout its use.

The mechanical properties of a desirable long-term skin, wound-care or biomedical adhesive are intimately related to its composition. An ideal candidate must maintain an aggressive adhesive nature throughout its use. This includes not only the short term needs of the user, but the adhesive must be durable after long-term storage. In ambient environments, an adhesive might experience a wide range of temperature cycles over extended periods of time. Subsequent chemical changes caused by reactions, such as further crosslinking or degradation, may weaken the pressure sensitive qualities of the adhesive system.

With regard to wound dressings and biomedical electrodes, a principle form of failure is due to the delamination of the adhesive from the wound. The adhesive must exhibit sufficient water vapor transmission to avoid excessive buildup of moisture within the adhesive, as well as to encourage the removal of moisture from the interface between the adhesive and the skin.

Pressure sensitive adhesives are known which are suitable for medical purposes. See, for example, U.S. Pat. Nos. 4,140,115; 4,310,509; 4,499,896; 4,685,455; 4,842,597; 4,871,812; 4,931,282; 5,045,601; 5,064,652; 5,088,483; 5,153,040; 5,160,315; 5,183,664; 5,296,512; 5,389,376; 5,407,717; and 5,468,821.

However, a need still exists to provide a pressure sensitive adhesive which exhibits high moisture absorbency and water vapor transmission rates, minimizes skin contamination, and retains both satisfactory structural integrity and skin adhesion in the presence of significant amounts of absorbed moisture. A need also exists to enhance the electrical conductivity of such adhesives while still maintaining desirable adhesive properties.

OBJECTS AND SUMMARY OF THE PRESENT INVENTION

It is thus one object of the present invention to provide a covalently crosslinked water-absorbent graft copolymer.

It is also an object of the present invention to provide a water-absorbent pressure sensitive adhesive suitable for use as a wound dressing.

It is further an object of the present invention to provide a water-absorbent pressure sensitive adhesive suitable for use as a medical adhesive.

It is yet further an object of the present invention to provide an electrically-conductive water-absorbent pressure sensitive adhesive suitable for use as a biomedical electrode.

In accordance with the present invention, there is thus provided a covalently crosslinked water-absorbent graft copolymer formed from one or more water-soluble base monomers A and a water-soluble or water-dispersible macromer C, and optionally one or more B monomers copolymerized with said A monomer, wherein said base monomer A comprises a vinyl monomer capable of forming a hydrophilic polymer and having a $T_g < 20°$ C., said optional monomer B being capable of forming a hydrophilic or hydrophobic polymer, and said C macromer forming polymeric sidechains of said graft copolymer, with the provisos that when said C macromer is present in an amount of at least 45 percent by weight, then at least 5 percent by weight of a B monomer having a $T_g > 20°$ C. is present, and when said C macromer is present in an amount of 35 percent by weight or less, then at least 5 percent by weight of a B monomer having a $T_g < 0°$ C. is present, and wherein any B monomer present, if hydrophobic, is present in an amount of 25 percent by weight or less, based on the total weight of the components A, B and C.

In accordance with a preferred embodiment of the present invention, the graft copolymer is formed from one or more water-soluble base monomers A and a water-soluble or water-dispersible macromer C, and optionally one or more B monomers copolymerizable with said A monomer, wherein said base monomer A comprises a vinyl monomer capable of forming a hydrophilic polymer and having a $T_g < 20°$ C., said optional monomer B is capable of forming a hydrophilic or hydrophobic polymer, and said macromer C forming polymeric sidechains of said graft copolymer and comprising a hydrophilic macromer represented by the formula:

$$X-(Y)_p-(O-C_mH_{2m})_n-R$$

wherein X is a moiety copolymerizable with monomers A and B or capable of attachment to polymerized monomers A and B, Y is a divalent linking group, R is a terminal group; and in which m is an integer of from 2 to 6, n is an integer of from 5 to 300, and p is 0 or 1.

In accordance with another preferred embodiment of the present invention, there is provided a covalently crosslinked pressure sensitive adhesive as described above which is also ionically-crosslinked by neutralization of functionalities within the polymer backbone or the macromer sidechains to an extent sufficient to enable the crosslinked graft copolymer to be electrically conductive or to enhance the water absorbency thereof.

In accordance with the present invention, there is also provided an adhesive composite suitable for use in a medical application such as a wound dressing, medical adhesive or biomedical electrode.

DETAILED DESCRIPTION OF THE INVENTION

The covalently crosslinked water-absorbent graft copolymer of the present invention comprises a graft copolymer of at least one water-soluble base monomer and a hydrophilic macromer. The covalently crosslinked graft copolymer exhibits acceptable pressure sensitive adhesive properties while retaining the ability of the copolymer to both transport moisture from the interface between the copolymer and the substrate by adsorption and to transport moisture (in the form of water vapor) through the copolymer layer to the atmosphere once absorbed.

The water-soluble base monomer A comprises a vinyl monomer capable of forming a hydrophilic polymer and having a $T_g < 20°$ C. In general, such monomers comprise hydroxy($C_{1-5}$)alkyl acrylates, hydroxy($C_{1-5}$)alkyl methacrylates, dihydroxy($C_{1-5}$)alkyl methacrylates, etc.. Exemplary water-soluble base monomers include but are not limited to hydroxyethyl acrylate, hydroxypropyl acrylate, hydroxybutyl acrylate, hydroxybutyl methacrylate, as well as alkyl vinyl ethers and hydroxy alkyl vinyl ethers (wherein the alkyl group has up to 5 carbon atoms). One or more of the water-soluble A monomers may be employed.

The macromer C forms polymeric sidechains on the graft copolymer. The macromer C is hydrophilic by nature (i.e., the macromer is water-soluble or water-dispersible).

The macromer may be represented by the formula X—(Y)$_p$—Z—R wherein X is a moiety copolymerizable with monomers A and B or, in the alternative, capable of attachment to polymerized monomers A and B, Y is a divalent linking group, Z is a water-soluble or water-dispersible homo- or polymeric moiety essentially unreactive at copolymerization conditions, R is a terminal group, and p is 0 or 1.

More specifically, the X moiety is an unsaturated polymerizable moiety the composition of which is not critical. The X moiety may be, for example, when intended to be copolymerizable with monomers A and B, simply a vinyl group of the formula CHR=CR$^1$— where R is hydrogen or COOH and R$^1$ is hydrogen or alkyl such as methyl. Other exemplary X moieties include but are not limited to methacryloyl, maleoyl, itaconoyl, crotonoyl, unsaturated urethane moiety, methacrylamido and moieties of the formula CH$_2$=CHCH$_2$O—.

The X moiety may comprise an amine or alcohol moiety (such as a monohydroxyl or monoamine moiety) which permits attachment of the macromer to a suitable functionality on previously-polymerized monomers A and B. For instance, the hydroxyl moiety can serve as a terminal reactive group by reaction with suitable moieties on the polymer backbone resulting from the use of monomers such as isocyanate-substituted (meth)acrylic acid, (meth)acrylic acid anhydride, etc.

A preferred Y divalent linking group is $$-\overset{O}{\underset{\|}{C}}-,$$

or a linking group which incorporates such a moiety.

Additional Y linking groups which may be employed in connection with the present invention include but are not limited to the following moieties:

$$-\overset{O}{\underset{\|}{C}}-O-;\ -O-\overset{O}{\underset{\|}{C}}-;\ -\overset{O}{\underset{\|}{C}}-NR-;\ -NR-\overset{O}{\underset{\|}{C}}-;$$

$$-\overset{O}{\underset{\|}{C}}-O-CR_2-CH_2-;\ -CH_2-O-CR_2-CH_2-;$$

$$-O-CR_2-CH_2-O-CR_2-CH_2-;$$

$$-OCH_2CH_2-O-CR_2-CH_2-;\ \text{and}$$

$$-\overset{O}{\underset{\|}{C}}-O-CH_2CH_2-NH-\overset{O}{\underset{\|}{C}}-O-CR_2-CH_2-;$$

where R is hydrogen, alkyl or phenyl. Obviously, the presence of the Y linking group is optional in the event the moiety includes a functionality which enables the Z moiety to react with the X moiety. As the incorporation of macromolecular moieties in copolymers is well understood by those skilled in the art, the choice of a suitable X and Y moiety for use in the present invention may be readily made upon practice of the present invention. See, for example, the discussion in U.S. Pat. Nos. 3,786,116; 3,832,423; 3,842,058; 3,842,059; 3,842,146; and 4,554,324, herein incorporated by reference.

The Z moiety is preferably selected from the group consisting of (but not limited to) a polypropylene or polyethylene oxide radical, a polyethyloxazoline radical such as a radical of poly(2-ethyl-2-oxazoline), polyacrylic acid radical, polyvinyl alcohol radical, polyvinylpyrrolidone radical, polyvinyl caprolactam radical, polymethylvinyl ether radical or mixtures thereof. Exemplary C macromers formed from such radicals include but are not limited to ethoxylated or propoxylated hydroxy($C_{1-5}$)alkyl meth (acrylate) and polymethylvinyl ether mono(meth)acrylate. The molecular weight of the macromer used in the present invention is not critical but will generally range from about 300 to about 50,000, and preferably from about 300 to 3,000.

The hydrophilic macromer C is more preferably represented by the formula:

$$X-Y-(O_{C_mH_{2m}})_n-R$$

wherein X and Y are as defined above and R represents a terminal group; and in which m is an integer of from 2 to 6 and n is an integer of from 5 to 300. More specifically, macromer C is advantageously an ethoxylated or propoxylated hydroxy($C_{1-5}$)alkyl (meth)acrylate represented by the formula:

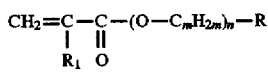

wherein $R_1$ is hydrogen or $C_{1-5}$ alkyl and R is a terminal group. Preferably, in is 2 or 3 and n is 5 to 30, and R is OH or $C_{1-5}$ alkyl.

The Z moiety is preferably comprised solely of one or more hydrophilic monomer radicals to ensure that the resulting macromer is water-soluble or water-dispersible. However, the Z moiety may also be a copolymer of hydrophilic and hydrophobic monomers, with any copolymerized hydrophobic portion being present in an amount insufficient to render the resulting macromer water-insoluble or non-water-dispersible. Desirably, any non-hydrophilic portion employed in such macromer is present in an amount of less than 50 percent by weight based on the weight of the macromer, and preferably less than 30 percent by weight.

The macromer C may employ a variety of terminal groups R. While the terminal group may typically be OH or $C_{1-5}$ alkyl, it may be desirable to select a terminal group based on the functional character of the terminal group. For instance, suitable terminal groups include but are not limited to (1) acid/ionic groups such as carboxyl, anhydride, phosphate or sulfate groups, (2) hydrophobic groups such as lower alkyl, phenyl or substituted phenyl, and (3) hydrophilic groups such as hydroxyl or amine groups.

As discussed above, one or more polymerizable B monomers may be incorporated in the copolymer which B monomer(s) is copolymerizable with the A monomer. Such additional B monomer(s) may be either hydrophilic or hydrophobic. The B monomer, if hydrophobic, is present in an amount of 25 percent by weight or less, and most preferably 20 percent by weight or less. In a preferred embodiment the B monomer is hydrophilic. In such an embodiment, the graft copolymer would contain no hydrophobic monomers.

Exemplary optional B monomers include water-soluble vinyl monomers having at least one nitrogen atom. Such monomers (each of which exhibit a $T_g$ of >20° C.) include but are not limited to N-mono-substituted acrylamides such as acrylamide, methacrylamide, N-methylacrylamide, N-ethylacrylamide, N-methylolacrylamide, N-hydroxyethylacrylamide, and diacetone acrylamide; N,N-disubstituted acrylamides such as N,N-dimethylacrylamide, N,N-diethylacrylamide, N-ethyl-N-aminoethyl acrylamide, N-ethyl-N-hydroxyethylacrylamide, N,N-dimethylolacrylamide, and N,N-dihydroxyethylacrylamide, etc.

Other optional B monomers may include, for example, various vinyl monomers such as acrylic and methacrylic acid, methoxyethyl acrylate or methacrylate, ethyoxyethyl acrylate or methacrylate, methyl acrylate or methacrylate, ethyl acrylate or methacrylate, propyl acrylate or methacrylate, glycerol acrylate or methacrylate, hydroxyethyl methacrylate, hydroxypropyl methacrylate, vinyl pyrrolidone and vinyl caprolactam (each of which also exhibit a $T_g$ of >20° C.). Monomeric acrylic or methacrylic acid esters of a non-tertiary alcohol having from 4–12 carbon atoms on average, and preferably from 4–8 carbon atoms, such as n-butyl acrylate or methacrylate, etc. are also suitable B monomers, with such monomers exhibiting a $T_g$ of <0° C. One or more B monomers may be employed.

Preferably, said A monomer is present in an amount of from 25 to 70 percent by weight, said optional B monomer is present in an amount of from 0 to 40 percent by weight (based on combined weights of hydrophilic and/or hydrophobic B monomers), and said C macromer is present in an amount of from 10 to 65 percent by weight, and preferably 30 to 60 percent by weight, based on the total weight of the respective components A, B and C in the composition. If both hydrophilic and hydrophobic B monomers are present, the amount of the hydrophobic B monomer present is preferably insufficient to exceed 25 percent by weight of the total weight of the monomers A, B and C.

Preferably, the composition contains at least about 35 percent by weight of the A monomer and at least about 30 percent by weight of the C macromer. Most preferably, at least about 40 percent by weight of the A monomer is present. Most preferably, at least 35 percent by weight of the C macromer is present.

By way of further proviso, when the C macromer is present in an amount of at least 45 percent by weight, it is preferred that at least 5 percent by weight of a B monomer having a $T_g$ of >20° C. is present, and when the C macromer is present in an amount of 35 percent by weight or less, it is preferred that at least 5 percent by weight of a B monomer having a $T_g$ of <0° C. is present.

If less than 30 percent by weight of the C macromer is employed, it may be necessary to incorporate a water-soluble tackifier or plasticizer into the composition to provide sufficient tack. Exemplary tackifiers include polyethylene glycol, polypropylene glycol, and suitable polyoxyethylene-based compounds. Suitable polyoxyethylene-based tackifiers are disclosed at column 6 of U.S. Pat. No. 4,413,080, herein incorporated by reference in its entirety. Such tackifiers, if present, may be employed in an amount of up to about 50 percent by weight, based on the total weight of the composition.

Most preferably, the weight ratio of C macromer to total weight of monomers A and B ranges from 35:65 to 65:35, with it being further preferred that the C macromer be present in a weight ratio of 40:60 to 50:50 based on the weight of C macromer to total weight of A and B monomers.

The weight average molecular weight of the resulting polymer is preferably at least 18,000, and may be as high as 100,000–200,000.

As noted above, the copolymer composition of the present invention may be prepared by any conventional polymerization technique, including (1) free radical initiated copolymerization of components A and C and optionally B in the presence of a solvent, and (2) attachment of the macromer C graft to a preformed backbone polymer formed from copolymerized monomer A optionally copolymerized with monomer B via reaction with a suitable functional group on the backbone polymer subsequent to formation of same. Suitable copolymerization temperatures range from about 20° C. to about 150° C. for periods of time of from 2 to 24 hours until the desired degree of conversion occurs.

Once the graft copolymer is prepared, the copolymer is covalently crosslinked by means of a suitable covalent crosslinking agent in a conventional manner. Suitable covalent crosslinking agents are well-known in the art. The crosslinking reaction which is contemplated is covalent by nature and may be achieved by incorporating into the polymerization mixture (for internal crosslinking) a polyfunctional ethylenically unsaturated compound in an amount sufficient to provide the desired crosslinking. External crosslinking agents may also be employed by admixture to the copolymer polymerization product.

Exemplary internal crosslinking agents suitable for addition to the reaction mixture include but are not limited to di- or triesters of (meth)acrylic acid, di- or poly-alkylene glycol (meth)acrylates, alkylene bis(meth)acrylamides and n-(isobutoxymethyl)acrylamide.

Exemplary external crosslinking agents which may be added to the polymerization product to provide the desired crosslinking include but are not limited to aziridines, titanates, melamine resins, etc.

Generally, the crosslinking agent is added to the reaction mixture or to the polymerization product in an amount of from 0.02 to about 2 percent by weight, preferably from about 0.05 to 1 percent by weight.

If it is desired to enhance the electrical conductivity or water absorption properties of the graft copolymer, the graft copolymer may be additionally ionically-crosslinked in a conventional manner. See, for example, the teachings of U.S. Pat. Nos. 3,264,272; 3,969,434; and 4,002,581 each herein incorporated by reference in their entirety.

The desired ionic crosslinking can occur by providing on at least a portion of the monomers A and B and/or the macromer C functional groups which are capable of being neutralized by a mono-, di- or trivalent metal ion. Exemplary functional groups are selected from the group consisting of carboxyl, sulfate, phosphate, anhydride and mixtures thereof. For example, at least one of the copolymerizable A monomers may comprise an ionically-crosslinkable monomer such as an alpha,beta-ethlenically unsaturated carboxylic acid group having from 3–8 carbon atoms, such as acrylic acid, methacrylic acid, ethacrylic acid, itaconic acid, maleic acid, fumaric acid, monoesters and dicarboxylic acids. Alpha,beta-monoethlenically unsaturated anhydrides of carboxylic acid such as maleic anhydride can also be employed. For example, from about 3 to 10 percent by weight of the total reactants A, B and C may comprise acrylic or (meth) acrylic acid to provide the desired functionalities.

It is also possible to employ an ionically-crosslinkable macromer in addition to the ionically-crosslinkable A monomer(s) discussed above. In such an embodiment, the macromer will incorporate an acidic/ionic terminal group such as carboxyl, sulfate, phosphate, anhydride or mixtures thereof.

As discussed in U.S. Pat. No. 3,264,272, the ionically-crosslinked graft copolymer of the present invention is produced by reaction of the copolymer with an ionizable metal compound in order to neutralize the appropriate functionalities (e.g., acid functionalities) on either the base monomers or on the macromer. Preferably, from about 2 to about 50 weight percent of the base monomers or the macromer contain functionalities which may be neutralized by reaction with an ionizable metal compound.

Metal ions which may be employed in the formation of the ionically-crosslinked graft copolymer include but are not limited to mono-, di- and trivalent ions of the metals of Groups I, II, III, IV and VIII. Suitable monovalent metal ions include sodium, potassium, lithium, cesium, silver, mercury and copper. Suitable divalent metal ions include beryllium, magnesium, calcium, strontium, berium, copper, cadmium, mercury, tin, lead, iron, cobalt, nickel and zinc. Suitable trivalent metal ions include aluminum, chromium, iron and yttrium. The preferred metal ions are alkali metal ions.

The crosslinking reaction (i.e., the neutralization of the appropriate neutralizable functionalities) is carried out by blending the graft copolymer with a solution of the crosslinking metal compounds in an amount sufficient to neutralize the neutralizable functionalities to the desired extent. Preferred metal compounds for use in providing the necessary neutralization include but are not limited to alkali and alkaline earth metal hydroxides. Also suitable are alkali metal salts or alkaline earth metal salts based on an organic acid, such as sodium acetate, calcium acetate, magnesium acetate, zinc formate, and zinc acetate.

The graft copolymer, if both covalently and ionically crosslinked, exhibits highly desirable water absorption, water vapor transmission, electrical conductivity and adhesive properties and thus serves as an optimum material for a biomedical electrode.

The resulting crosslinked copolymer may be used in solution form. Preferably, the copolymer is applied to a backing material (such as a tape) in solution form, with the solvent being removed upon application to the tape. The copolymer is applied in a thickness sufficient to provide the desired adhesion together with the desired degree of water absorption. Suitable copolymer layer thicknesses range from a few microns to 5m m or so, such as from 10 to 100 microns. Advantageously, the thickness of the layer does not affect the water vapor transmission capability of the copolymer.

Exemplary backing materials include but are not limited to flexible and inflexible backing materials conventionally employed in the area of pressure sensitive adhesives, such as creped paper, kraft paper, fabrics (knits, non-wovens, wovens), foil and synthetic polymer films such as polyethylene, polypropylene, polyvinyl chloride, poly (ethylene terephthalate) and cellulose acetate, as well as glass, ceramics, metallized polymer films and other compatible sheet or tape materials. Advantageously, the backing material is permeable to water vapor to enhance the water vapor transmission rate through the material and exhibits water absorbent properties.

The backing material may be of any desired shape and configuration, such as adhesive tapes, strips, wound dressings, surgical drapes, biomedical electrodes, etc. It may be desirable to include a dressing or absorbent pad attached to the copolymer layer. Such materials may be coated in any conventional manner with the copolymer of the present invention, such as by roll coating, spray coating, extrusion coating, co-extrusion coating, hot melt coating by use of conventional coating devices. When appropriate, the copolymer of the present invention may be applied as a solution and the solvent subsequently removed to leave a tacky adhesive residue on the backing material.

The water-absorbent copolymer of the present invention may be used in a wide variety of commercial applications. For example, the crosslinked water-absorbent copolymer of the present invention may be used as a skin adhesive for adhesive tapes and bandages, as a wound dressing, as a burn dressing, as a sealant coating on catheters or other medical devices, etc.

When used as a wound dressing, the covalently crosslinked graft copolymer of the present invention may include a suitable medicament such as antibacterials, antiseptics, antibiotics, nutrients, anaesthetics, analgesics, anti-inflammatories, etc. Such agents may be incorporated as a dispersed solid, in the form of a solution in admixture with the reactant monomer components prior to polymerization, or added to the crosslinked copolymer in the form of an absorbed aqueous solution (e.g., buffered or physiological saline) of the medicament. The covalently crosslinked graft copolymer is permeable to the incorporated medicament and can thus serve as a sustained release device. Exemplary antimicrobial agents include but are not limited to iodine, chlorhexidene gluconate, parachlorometaxylenol, bacitracin salts, neomycin sulfate, silver sulfadiazine, polymyxin B sulfate, etc.

Advantageously, the covalently crosslinked copolymer of the present invention may also be foamed to provide a highly water absorbent foamed layer for use in absorbent pads or similar articles. Such foams may be formed by conventional means, such as by adding a blowing or expanding agent (e.g., dichlorodifluoromethane or dichlorotetrafluoroethane) to the copolymer and subsequently causing the formation of a foam layer on a coated substrate of desired thickness and porosity.

Alternatively, the admixture of blowing agent and crosslinked copolymer can be injection molded to produce a molded foam article of desired shape which exhibits high water absorbency and water vapor transmission.

It is an advantage of the present invention that the crosslinked graft copolymer of the present invention exhibits a water vapor transmission rate of at least 900 grams/m$^2$/24 hours at 40° C. and at 80% relative humidity differential. Preferably, the crosslinked graft copolymer of the present invention exhibits a water vapor transmission rate of from 1000 to 4000 grams/m$^2$/24 hours, while still exhibiting satisfactory adhesive properties.

The invention will be discussed in conjunction with the following examples, which are merely illustrative of the present invention and not intended to in any way limit the scope of the invention.

EXAMPLE 1

180.13 grams of ethyl acetate and 120.09 grams of isopropyl alcohol (as solvents) were charged to a 1-liter reaction vessel. To the charged material, 18.33% of the monomers identified below were added. Under a nitrogen atmosphere, the batch was heated to 71°–77° C. and 1.27 grams of VAZO-52 (polymerization initiator) were added. The reactants were allowed to polymerize for 20 minutes to produce a seed polymer capable of solvating the remaining reactants. The remaining 81.67% of the monomer mix along with 0.75 grams of benzoyl peroxide were added to the reaction mix over 2 hours while maintaining a reaction temperature of 71°–77° C. The reactants were polymerized until all monomers were consumed. The reactor feed mix consisted of the following components:

|  | Amount (Grams) |
| --- | --- |
| Monomers |  |
| HEMA-10 (macromer) | 114.09 |
| HEMA-5 (macromer) | 26.34 |
| Hydroxy Ethyl Acrylate (A monomer) | 83.88 |
| Hydroxy Propyl Acrylate (A monomer) | 100.67 |
| Acrylamide (B monomer) | 9.06 |
| Solvents |  |
| Ethyl acetate | 180.13 |
| Isopropyl alcohol | 120.09 |

Note:

HEMA-5,10 are 5 and 10 mole ethoxylates of hydroxy ethyl methacrylate (produced by BIMAX, INC.)

VAZO-52: Dupont trade name for free radical initiatoris 2,2'-azobis (2,4-dimethylpentanenitrile).

The resulting copolymer may be covalently crosslinked by use of a suitable crosslinking agent.

EXAMPLE 2

The procedure of Example 1 was repeated using the following reactor feed components to produce a graft copolymer which may be crosslinked by addition of a suitable crosslinking agent to form a crosslinked absorbent copolymer:

|  | Amount (Grams) |
| --- | --- |
| Monomers |  |
| HEMA-10 (macromer) | 134.22 |
| Hydroxy Ethyl Acrylate (A monomer) | 97.31 |
| Acrylamide (B monomer) | 9.06 |
| Butyl Acrylate (B monomer) | 57.04 |
| Vinyl Pyrrolidone (B monomer) | 20.13 |
| Acrylic Acid (B monomer) | 13.42 |
| Solvents |  |
| Ethyl acetate | 150.11 |
| Isopropyl alcohol | 150.11 |

EXAMPLE 3

The procedure of Example 1 was repeated using the following reactor feed components to produce a graft copolymer which may be crosslinked by addition of a suitable crosslinking agent to form a crosslinked absorbent copolymer:

|  | Amount (Grams) |
| --- | --- |
| Monomers |  |
| HEMA-10 (macromer) | 113.50 |
| Hydroxy Ethyl Acrylate (A monomer) | 107.38 |
| Acrylamide (B monomer) | 6.56 |
| Butyl Acrylate (B monomer) | 54.73 |
| Vinyl Pyrrolidone (B monomer) | 40.25 |
| Acrylic Acid (B monomer) | 13.12 |
| Solvents |  |
| Ethyl acetate | 180.13 |
| Isopropyl alcohol | 120.09 |

EXAMPLE 4

The procedure of Example 1 was repeated using the following reactor feed components to produce a graft copolymer which may be crosslinked by addition of a suitable crosslinking agent to form a crosslinked absorbent copolymer:

|  | Amount (Grams) |
| --- | --- |
| Monomers |  |
| HEMA-10 (macromer) | 134.22 |
| Hydroxy Ethyl Acrylate (A monomer) | 97.31 |
| Hydroxy Propyl Acrylate (A monomer) | 40.27 |
| Acrylamide (B monomer) | 10.06 |
| Butyl Acrylate (B monomer) | 23.56 |
| Vinyl Pyrrolidone (B monomer) | 10.06 |
| Acrylic Acid (B monomer) | 10.06 |
| Solvents |  |
| Ethyl acetate | 160.11 |
| Isopropyl alcohol | 140.11 |

EXAMPLE 5

The procedure of Example 1 was repeated using the following reactor feed components to produce a graft copolymer which may be crosslinked by addition of a suitable crosslinking agent to form a crosslinked absorbent copolymer:

| Monomers | Amount (Grams) |
|---|---|
| HEMA-10 (macromer) | 268.43 |
| Hydroxy Ethyl Acrylate (A monomer) | 181.20 |
| Hydroxy Propyl Acrylate (A monomer) | 181.20 |
| Acrylamide (B monomer) | 20.13 |
| Acrylic Acid (B monomer) | 20.13 |
| Solvents | |
| Ethyl Acetate | 345.25 |
| Isopropyl Alcohol | 255.19 |

EXAMPLE 6

The following procedure was used to form a graft copolymer which may be crosslinked by addition of a suitable crosslinking agent to form a crosslinked absorbent copolymer.

94.5 grams of ethyl acetate and 130.5 grams of isopropyl alcohol (or solvents) were charged to a 1-liter reaction vessel. To the charge, 18.33% of the monomers identified below were added. Under a nitrogen atmosphere, the batch was heated to 71°–77° C. and 0.94 grams of VAZO-52 (polymerization initiator) were added. The reactants were allowed to polymerize for 20 minutes. The remaining 81.67% of the monomer mix along with 0.50 grams of benzoyl peroxide were added to the reaction mix over 1 hour while maintaining a reaction temperature of 71°–77° C. The reactants were polymerized until all monomers were consumed (123.75 grams of isopropyl alcohol were added to reduce viscosity). The monomer feed consisted of the following:

| Monomers | % of Monomers | Amount (Grams) |
|---|---|---|
| HEMA-10 (macromer) | 38.13 | 90.00 |
| 2-Ethyl-2-Oxazoline (macromer) | 4.66 | 11.00 |
| Hydroxy Ethyl Acrylate (A monomer) | 23.83 | 56.25 |
| Hydroxy Propyl Acrylate (A monomer) | 10.97 | 25.88 |
| Vinyl Pyrrolidone (B monomer) | 4.77 | 11.25 |
| Vinyl Caprolactam (B monomer) | 4.77 | 11.25 |
| Butyl Acrylate (B monomer) | 12.87 | 30.37 |

The presence of the 2-ethyl-2-oxazoline macromer (5000 mw) enhanced the cohesive strength of the graft copolymer.

EXAMPLE 7

The procedure of Example 6 was repeated with the exception that the 2-ethyl-2-oxazoline macromer was not employed:

| Solvents | Amount (Grams) |
|---|---|
| Ethyl Acetate | 189.00 |
| Isopropyl Alcohol | 261.00 |

| Monomers | % of Monomers | Amount (Grams) |
|---|---|---|
| HEMA-10 (macromer) | 40.00 | 179.98 |
| Hydroxy Ethyl Acrylate (A monomer) | 25.00 | 12.50 |
| Hydroxy Propyl Acrylate (A monomer) | 11.50 | 52.29 |
| Vinyl Pyrrolidone (B monomer) | 5.00 | 22.55 |
| Vinyl Caprolactam (B monomer) | 5.00 | 22.55 |
| Butyl Acrylate (B monomer) | 13.50 | 60.76 |

EXAMPLE 8

Ethyl acetate (25 grams) and isopropyl alcohol (75 grams) (as solvents) were charged to a reaction vessel. To the charge, 19.86% of the monomers identified below were added. Under a nitrogen atmosphere, the batch was heated to 70°–73° C. and 0.94 grams of VAZO-52 (polymerization initiator) were added together with 100 grams of additional solvent mixture. The reactants were allowed to polymerize for 20 minutes. The remaining 80.14% of the monomer mix along with benzoyl peroxide catalyst were added to the reaction mix over 1 hour while maintaining a reaction temperature of 70°–73° C. The reactants were polymerized until all monomers were consumed. The monomer feed consisted of the following:

| Monomers | % of Monomers | Amount (Grams) |
|---|---|---|
| HEMA-10 (macromer) | 40.00 | 90.00 |
| HEMA-5 (macromer) | 5.00 | 11.00 |
| Hydroxy Ethyl Acrylate (A monomer) | 22.75 | 56.25 |
| Hydroxy Propyl Acrylate (A monomer) | 8.75 | 25.88 |
| Vinyl Pyrrolidone (B monomer) | 3.50 | 11.25 |
| Vinyl Caprolactam (B monomer) | 3.50 | 11.25 |
| Butyl Acrylate (B monomer) | 15.00 | 30.37 |
| Acrylic acid (B monomer) | 1.50 | |

Upon completion of the reaction, the reaction product is cooled and discharged from the reactor. Before coating on a backing material, 0.15% a crosslinking agent (an aziridine compound such as Hoechst Celanese XAMA-7) is added to the graft copolymer and crosslinking caused to occur upon addition to the copolymer at ambient conditions whereby a crosslinked absorbent graft copolymer is produced. The moisture vapor transmission rate (MVTR) of the thus-produced graft copolymer is determined to be approximately 1800 gm/m$^2$/day while exhibiting an adhesive peel adhesion of 48 oz.

What is claimed is:

1. An covalently crosslinked water-absorbent graft copolymer comprising the copolymerization reaction product of one or more water soluble base monomers A and water soluble or water dispersible macromer C, and optionally one or more B monomers copolymerized with said A monomer, wherein said base monomer A consists of a vinyl monomer capable of forming a hydrophilic polymer and having a Tg<20° C., said optional monomer B being different from monomer A and capable of forming a hydrophilic or hydrophobic polymer, and said C macromer forming polymeric sidechains on said graft copolymer and defined by the formula X—(Y)$_p$—Z—R, wherein X is a moiety copolymerizable with monomers A and B or capable of attachment to copolymerized monomers A and B, Y is a divalent linking group, Z is a water-soluble or water-dispersible homo- or copolymeric moiety, R is a terminal group, and p is 0 or 1, with the provisos that when said C macromer is present in an amount of at least 45 percent by weight, then at least 5 percent by weight of a B monomer having a Tg of >20° C. is present, and when said C macromer is present in an amount of 35 percent by weight or less, then at least 5 percent by weight of a B monomer having a Tg of <0° C. is present, and wherein any B monomer present, if hydrophobic, is present in an amount up to 25 percent by weight, each said amounts being based on the total weight of the components A, B and C.

2. The crosslinked copolymer of claim 1 wherein said A monomer is present in an amount of from 25 to 70 percent by weight, said B monomer is present in an amount of from 0 to 40 percent by weight, and said C macromer is present in an amount of from 10 to 65 percent by weight, based on the total weight of the respective components A, B and C.

3. The crosslinked copolymer of claim 1 wherein said C macromer is present in an amount of at least 35 percent by weight.

4. The crosslinked copolymer of claim 1 wherein the weight ratio of C macromer to monomers A and B present in said adhesive ranges from about 35:65 to 65:35.

5. The crosslinked copolymer of claim 4 wherein the weight ratio of C macromer to monomers A and B present in said adhesive ranges from about 40:60 to 50:50.

6. The crosslinked copolymer of claim 1 wherein said B monomer is hydrophilic.

7. The crosslinked copolymer of claim 1 wherein said A monomer is selected from the group consisting of hydroxy ($C_{1-5}$)alkyl acrylates, hydroxy($C_{1-5}$)alkyl methacrylates, dihydroxy($C_{1-5}$)alkyl acrylates, dihydroxy($C_{1-5}$)alkyl methacrylates and mixtures thereof.

8. The crosslinked copolymer of claim 1 wherein said B monomer is a water-soluble vinyl monomer having at least one nitrogen atom.

9. The crosslinked copolymer of claim 8 wherein said B monomer is selected from the group consisting of N-monosubstituted acrylamides, N,N-disubstituted acrylamides and mixtures thereof.

10. The crosslinked copolymer of claim 1 wherein X is a (meth)acrylate moiety.

11. The crosslinked copolymer of claim 1 wherein Z is selected from the group consisting of a polyalkylene oxide radical, a polyethyloxazoline radical, a polyacrylic acid radical, a polyvinyl alcohol radical, a polyvinylpyrrolidone radical, a polyvinylcaprolactam radical and a polymethylvinyl ether radical.

12. The crosslinked copolymer of claim 1 wherein said macromer is defined by the formula:

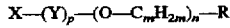

$$X-(Y)_p-(O-C_mH_{2m})_n-R$$

wherein X is a moiety copolymerizable with monomers A and B or capable of attachment to copolymerized monomers A and B, Y is a divalent linking group, R is a terminal group, m is an integer of from 2 to 6, n is an integer of from 5 to 300, and p is 0 or 1.

13. The crosslinked copolymer of claim 12 wherein the macromer is defined by the formula

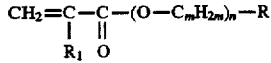

$$CH_2=C-C-(O-C_mH_{2m})_n-R$$
$$\phantom{CH_2=}|\phantom{-}\|$$
$$\phantom{CH_2=}R_1\phantom{-}O$$

wherein $R_1$ is hydrogen of $C_{1-5}$ alkyl and R is a terminal group.

14. The crosslinked copolymer of claim 12 wherein R is OH or $C_{1-5}$ alkyl.

15. The crosslinked copolymer of claim 12 wherein n is an integer of from 5 to 30.

16. The crosslinked copolymer of claim 1 wherein said macromer is selected from the group consisting of ethoxylated hydroxyethyl (meth)acrylate and ethoxylated hydroxypropyl (meth)acrylate.

17. The crosslinked copolymer of claim 1, wherein said B monomer is a vinyl monomer selected from the group consisting of acrylic acid, methacrylic acid, methoxyethyl acrylate, methoxyethyl methacrylate, ethoxyethyl acrylate, ethoxyethyl methacrylate, methyl acrylate, methyl methacrylate, ethyl acrylate, ethyl methacrylate, propyl acrylate, propyl methacrylate, n-butyl acrylate, n-butyl methacrylate, vinyl pyrrolidone, vinyl caprolactam and mixtures thereof.

18. The crosslinked copolymer of claim 1 wherein said macromer is selected from the group consisting of ethoxylated hydroxy ($C_{1-5}$ alkyl) acrylate, propoxylated hydroxy ($C_{1-5}$ alkyl) acrylate, ethoxylated hydroxy ($C_{1-5}$ alkyl) methacrylate and propoxylated ($C_{1-5}$ alkyl) methacrylate.

19. The crosslinked copolymer of claim 1 wherein said macromer is selected from the group consisting of ethoxylated and propoxylated hydroxy ($C_{1-5}$ alkyl) (meth)acrylate, poly(2-ethyl-2-oxazoline), polyacrylic acid, polyvinyl alcohol, polyvinyl pyrrolidone, polyvinyl caprolactam and polymethylvinyl ether mono (meth)acrylate.

20. The crosslinked copolymer of claim 1 wherein at least a portion of at least one of said base monomers A and B and macromer C include a functionality which is neutralized by a mono-, di- or trivalent metal ion.

21. The crosslinked copolymer of claim 20 wherein said functionality is selected from the group consisting of carboxyl, sulfate, phosphate, anhydride and mixtures thereof.

22. The crosslinked copolymer of claim 20 wherein from about 50 to about 100 percent of said functionalities are neutralized.

23. The crosslinked copolymer of claim 20 wherein said B monomer comprises (meth)acrylic acid in an amount ranging from about 3 to about 10 percent by weight based on the total weight of components A, B and C.

24. The crosslinked copolymer of claim 20 wherein at least a portion of said macromer C includes terminal groups which are neutralized by a mono-, di- or trivalent metal ion.

25. The crosslinked copolymer of claim 24 wherein said terminal groups which are neutralized are selected from the group consisting of carboxyl, sulfate, phosphate, anhydride and mixtures thereof.

26. The crosslinked copolymer of claim 20 wherein at least a portion of at least one of said monomers A and B and said macromer C include functionalities which are neutralized by a mono-, di- or trivalent metal ion.

* * * * *